US008057759B2

(12) United States Patent
Lee et al.

(10) Patent No.: US 8,057,759 B2
(45) Date of Patent: Nov. 15, 2011

(54) MICROFLUIDIC SYSTEM AND APPARATUS AND METHOD OF CONTROLLING THE SAME

(75) Inventors: Jeong-gun Lee, Yongin-si (KR);
Yoon-kyoung Cho, Yongin-si (KR);
Beom-seok Lee, Yongin-si (KR);
Jong-myeon Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1133 days.

(21) Appl. No.: 11/835,461

(22) Filed: Aug. 8, 2007

(65) Prior Publication Data
US 2008/0058991 A1 Mar. 6, 2008

(30) Foreign Application Priority Data
Sep. 5, 2006 (KR) .................. 10-2006-0085373

(51) Int. Cl.
*B01L 3/02* (2006.01)
*B01L 3/00* (2006.01)
*G01N 15/06* (2006.01)
*G01N 33/00* (2006.01)

(52) U.S. Cl. ....... 422/509; 422/502; 422/503; 422/68.1; 422/506; 436/43; 436/177; 436/180

(58) Field of Classification Search .............. 422/502, 422/503, 68.1, 50, 506, 509; 436/43, 177, 436/180
See application file for complete search history.

(56) References Cited

U.S. PATENT DOCUMENTS

| 4,746,849 | A | 5/1988 | Rosshirt |
| 5,449,621 | A | 9/1995 | Klein |
| 6,013,513 | A | 1/2000 | Reber et al. |
| 6,563,584 | B1 | 5/2003 | Yurino et al. |
| 2002/0090641 | A1 | 7/2002 | Yasuda et al. |
| 2002/0135754 | A1 | 9/2002 | Gordon |
| 2002/0137218 | A1 | 9/2002 | Mian et al. |
| 2003/0156763 | A1* | 8/2003 | Soderman ............ 382/262 |
| 2003/0156991 | A1 | 8/2003 | Halas et al. |
| 2006/0085160 | A1 | 4/2006 | Ouchi |
| 2008/0213904 | A1* | 9/2008 | Sliwa et al. ............ 436/56 |

FOREIGN PATENT DOCUMENTS

| EP | 1 324 042 A2 | 7/2003 |
| EP | 1 491 875 A1 | 12/2004 |
| EP | 1584917 A2 | 10/2005 |
| WO | 9853311 A2 | 11/1998 |
| WO | 0102737 A1 | 1/2001 |

* cited by examiner

*Primary Examiner* — Brian J Sines
(74) *Attorney, Agent, or Firm* — Sughrue Mion, PLLC

(57) ABSTRACT

Provided are an apparatus and a method of controlling a microfluidic system, and the microfluidic system. The apparatus of controlling the microfluidic system includes a central control block controlling an operation of the microfluidic system, a rotator control block controlling a rotator, a position control block controlling the position of a moving unit, the moving unit moving to a position of the microfluidic structure, and a radiation energy source control block controlling energy of a radiation energy source, the radiation energy source using an electromagnetic wave to scan over a position of the microfluidic structure. Such a configuration allows effective control of a miniaturized portable microfluidic system.

8 Claims, 13 Drawing Sheets

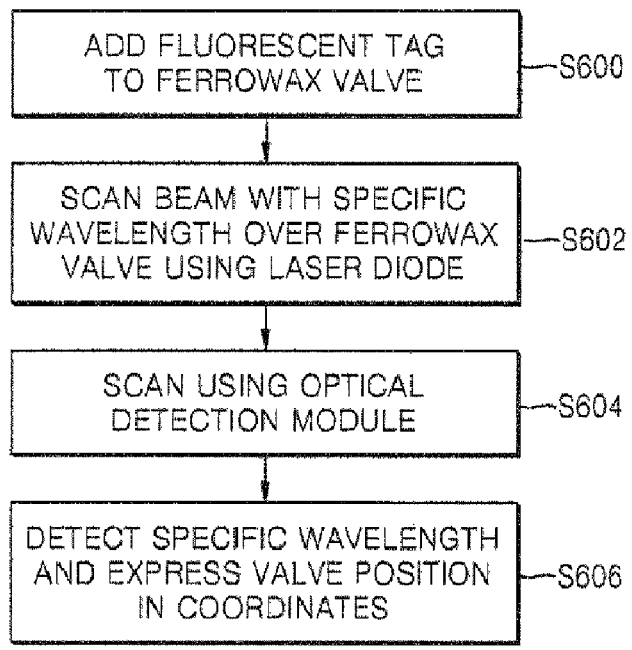
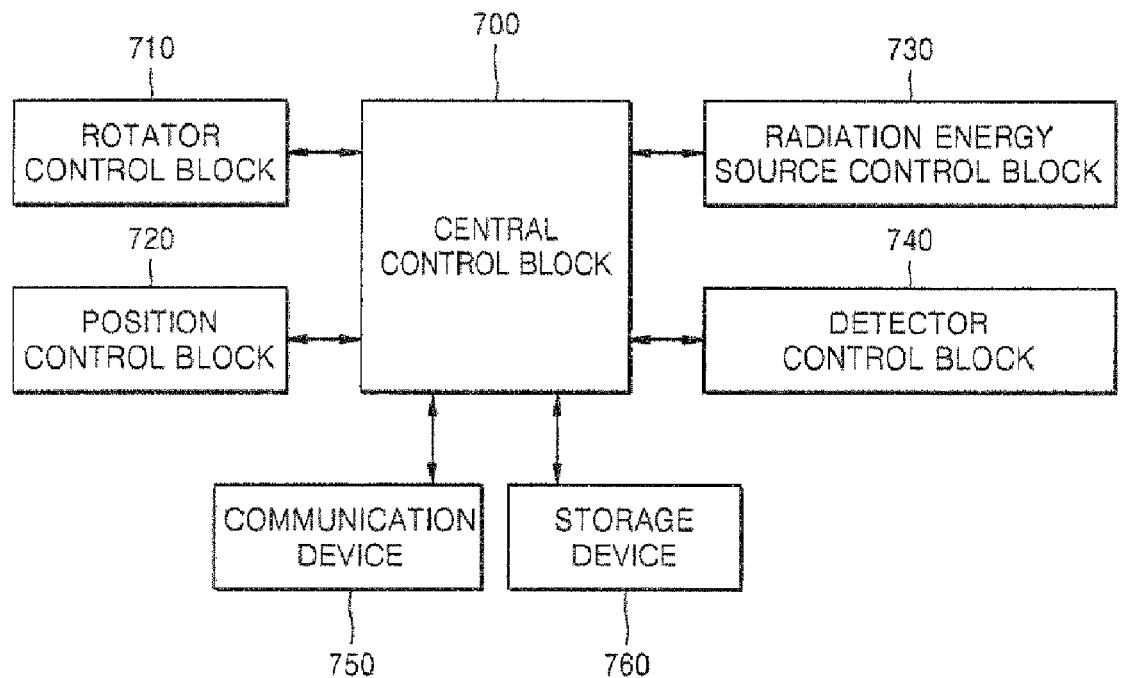

MICROFLUIDIC SYSTEM AND APPARATUS AND METHOD OF CONTROLLING THE SAME

CROSS-REFERENCE TO RELATED PATENT APPLICATION

This application claims the benefit of Korean Patent Application No. 10-2006-0085373, filed on Sep. 5, 2006, in the Korean Intellectual Property Office, the disclosure of which is incorporated herein in its entirety by reference.

BACKGROUND OF THE INVENTION

1. Field of the Invention

The present invention relates to an apparatus for controlling a microfluidic system and a control method thereof The present invention relates to a microfluidic system that allows a series of biochemical procedures, starting from an extraction of a target cell or genetic material (e.g. deoxyribonucleic acid (DNA)) from a biological sample to an amplification of the genetic material, and to a biochemical reaction employing the amplified genetic material.

2. Description of the Related Art

Generally, a microfluidic structure that composes a microfluidic apparatus or device includes a chamber for containing a trace amount of fluid, a channel through which fluid flows, a valve that can control a flow of fluid, and functional units that can perform various functions, such as chemical or biological reactions, separation, purification and detection of a target substance, on the fluid. A biochip is a structure that is obtained by arranging a plurality of such microfluidic structures on a chip-type substrate in order to perform various assays including biological and biochemical reactions using the microfluidic structures on a chip. Particularly, a device that is designed to perform multiple steps of processes and operations using a single chip is called a lab-on-a chip.

A driving pressure is generally required to transfer fluid within a microfluidic structure. A capillary pressure is one example of the driving pressure. In some cases, a pressure generated by a specifically prepared pump is used as the driving pressure. A lab-on-a compact disk (CD) is a recently introduced microfluidic device that is obtained by arranging microfluidic structures on a compact disk-shaped rotary body and uses centrifugal force. However, due to the characteristic of a rotary body that is usually not affixed to a frame but is instead free to move, controlling a fluid flow or temperature within a lab-on-a CD may be difficult.

SUMMARY OF THE INVENTION

The present invention provides a microfluidic system employing a centrifugal force to derive fluid to flow through microfluidic structures in the system, in which a fluid flow and various functions in respective microfluidic structures are controlled. The system may be used for performing a series of biochemical procedures which starts from a separation of a target cell from a biological sample, to an extraction of a nucleic acid from the target cell, to an amplification of the nucleic acid, and to a biochemical reaction using the amplified nucleic acid.

The present invention also provides an apparatus and a method of controlling a microfluidic system using a centrifugal force, magnetic force and indirect heat.

According to an aspect of the present invention, there is provided an apparatus for controlling a microfluidic system, wherein the microfluidic system comprises a microfluidic device in which a microfluidic structure is arranged on a rotary body; a rotator which rotates the rotary body; a moving unit which moves from a first position to a second position of the microfluidic device; and an energy source, the apparatus comprising:

a central control block which controls operation of the microfluidic system;

a rotator control block which controls the rotator in response to a first control signal from the central control block, a position control block which controls a position of the moving unit in response to a second control signal from the central control block; and an energy source control block which controls an emission of energy from the energy source in response to a third control signal from the central control block, wherein the energy source emits an electromagnetic wave.

According to another aspect of the present invention, there is provided a microfluidic system including a centrifugal force-driven microfluidic device, a rotator, an energy source, a detector, a moving unit, and a control apparatus; wherein the control apparatus comprises a central control block which controls operation of the microfluidic system;

a rotator control block which controls the rotator in response to a first control signal from the central control block, a position control block which controls a position of the moving unit in response to a second control signal from the central control block; and an energy source control block which controls an emission of energy from the energy source in response to a third control signal from the central control block, wherein the energy source emits an electromagnetic wave; and wherein the microfluidic device comprises a symmetrical rotary body, at least two units placed on the rotary body and a microfluidic structure; in which the microfluidic structure transfers a target substance along a path between the two units, and comprises heat generating particles which emit heat upon application of energy and a heat activation unit which is activated by the heat emitted by the heat generating particles;

wherein the rotator rotates the rotary body and causes a fluid sample to flow by a centrifugal force generated by a rotation of the rotary body;

the energy source uses an electromagnetic wave to scan the heat generating particles without contacting the microfluidic structure;

the detector detects optical information related to a reaction of the fluid sample in the microfluidic structure; and the moving unit moves from a first position to a second position of the microfluidic device.

In one embodiment, the detector performs a detection of an electromagnetic wave of a desired wavelength emitted from the heat generating particles and outputs a result of the detection to the control apparatus, and the control apparatus computes a position of the heat generating particles based on the detection of the electromagnetic wave of the desired wavelength.

According to another aspect of the present invention, there is provided a method of controlling the microfluidic system, the method including controlling the rotator, the moving unit, the energy source to perform a reaction of the fluid sample, controlling the detector to detect optical information related to the reaction of the fluid sample, and analyzing the fluid sample based on the detected optical information.

According to another aspect of the present invention, there is provided a method of controlling the operation of a valve of a microfluidic structure, wherein a microfluidic system includes a microfluidic device in which the microfluidic structure is arranged on a disk-shaped rotary body and wherein the microfluidic system comprises a microfluidic device in which the microfluidic structure is arranged on a disk-shaped rotary body and wherein the microfluidic device comprises an energy source which moves in a direction of a radius of the rotary body and emits an electromagnetic wave of a first wavelength, the method comprising: rotating the rotary body to move the valve to a position in proximity to the energy source; moving the energy source toward the valve; and applying the electromagnetic wave of the first wavelength to the valve to open or close the valve.

In one embodiment, the controlling method further comprises, prior to the rotating of the rotary body, automatically detecting a position of the valve, by adding a material emitting an electromagnetic wave of a second wavelength which differs from the first wavelength to the valve; scanning the electromagnetic wave of the first wavelength over the valve using the energy source; detecting the electromagnetic wave of the second wavelength emitted from the material; and computing the position of the valve based on a location of the electromagnetic wave of the second wavelength.

According to a further aspect of the present invention, there is provided a computer readable recording medium implemented with a program to perform the above methods in a computer.

Detailed features and advantages of the present invention are described in the appended dependent claims.

BRIEF DESCRIPTION OF THE DRAWINGS

The above and other features and advantages of the present invention will become more apparent by describing in detail exemplary embodiments thereof with reference to the attached drawings in which:

FIG. 6 is a flowchart for describing a method of automatically detecting a position of a target substance/target unit of the microfluidic structure to which an energy is applied;

FIG. 7 illustrates a block diagram of an apparatus for controlling a microfluidic system according to an embodiment of the present invention;

DETAILED DESCRIPTION OF THE INVENTION

Figure 1:
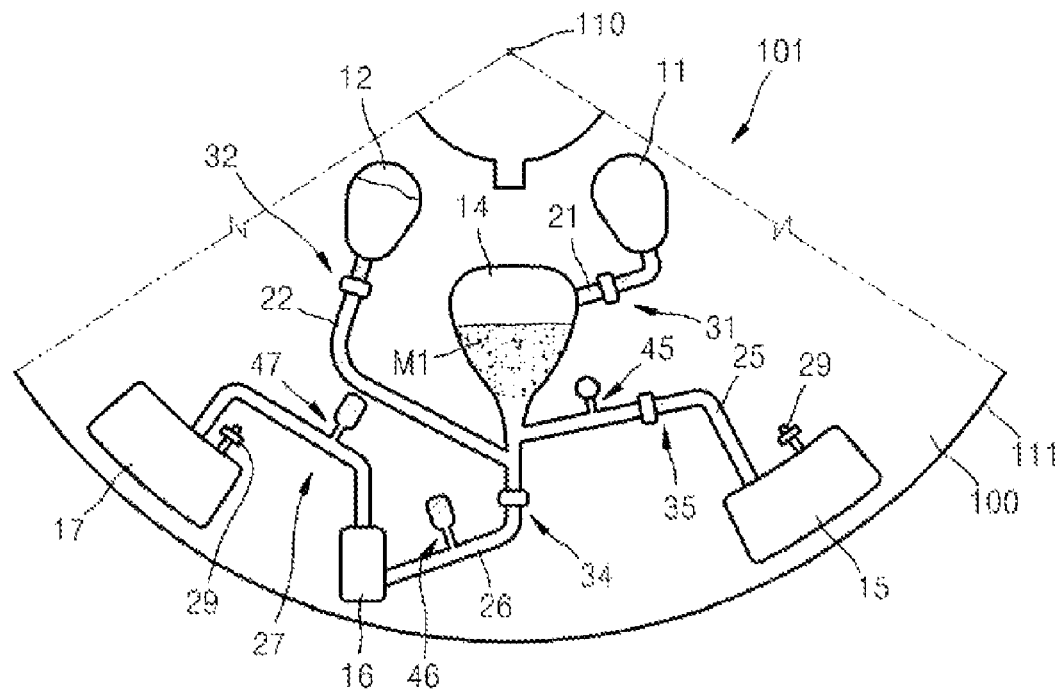
FIG. 1 illustrates a simplified top view of a microfluidic apparatus for extracting nucleic acids according to a first embodiment of the present invention.

The microfluidic device comprises one or more microfluidic or microchannel structures having an inlet port for application of a liquid sample and an outlet port for release the liquid sample or reaction products after various reactions or treatments. There may also be separate inlet ports for application of solvents and reagents and separate outlet ports or waste chambers/cavities for withdrawal of other components that are added and/or produced in the structure. Two or more microchannel structures may have common inlet ports.

Microfluidic device typically comprise one, two or more, microchannel structures fabricated wholly or partly in the surface of a planar substrate. In one embodiment, the side of the substrate in which the microchannels are located (microchannel side) may be covered by a lid comprising remaining parts, if any, of the microchannel structure. When the lid is properly mated to the upper side of the substrate, parts of the microchannel structures in the lid, if any, match the structures in the microchannel side thereby completing the microchannel structures of the device. In one embodiment, the lid may be transparent so that the reactions or samples inside the structures may be observed outside.

The microfluidic apparatus or devices have an axis of symmetry. For example, they may be disc-formed and have various geometries, with the circular form being the preferred variant (CD-form). Other variants of discs may have an axis of symmetry that is at least 3- or at least 6-numbered.

On CD-shaped device, each microchannel structures may be oriented radially around a central axis with an intended flow direction for each structure from an inner application area (inlet port) towards the periphery of the disc. The arrangement may be in form of one or more concentric circles (annular/circular arrangements). In an embodiment of the present invention, the fluid is transported by inertia force, for instance centrifugal force, in at least a part of a microchannel structure. Examples of other ways of transportation are by capillary action, hydrodynamically, magnetic, indirect heat, etc. These alternatives may also be combined with inertia force to transfer the fluid or solid substances.

Each microfluidic device comprises one or more structures such as channels and cavities (chambers) in the microformat. Different parts of a structure may have different discrete functions. In addition to the channel parts to introduce a biological sample and to transport the sample, there may be one or more channel/chamber parts that function as (a) application zone/port for reagents, magnetic microparticles, and liquids other than sample liquid, (b) reaction zone, for instance for reactions (e.g., polymerase chain reaction, etc).

(c) mixing zone, (d) zone for separating and/or concentrating and/or purifying the target substance (such as nucleic acid or a cell) or a derivative or fragment thereof, for instance by capillary electrophoresis, chromatography and the like, (e) waste conduit/chamber/cavity (for instance in the form of an outlet port), (f) zone for splitting a liquid flow, etc.

Between parts having different functions there may be valves that control the fluid flow. Various types and operations of valves in microfluidic systems are known. E.g., WO 9853311 (Gamera Bioscience) and WO 0102737 (Gyros AB)), of which contents are incorporated by reference.

The present invention will now be described more fully with reference to the accompanying drawings, in which exemplary embodiments of the invention are shown.

FIG. 1 illustrates a simplified top view of a microfluidic device for extracting nucleic acids according to a first embodiment of the present invention. The microfluidic device 101 includes a rotary body 100. In FIG. 1, the rotary body 100 has a circular disk-shape as a symmetrical shape, but the symmetrical shape is not limited to a disk-shape. One or more microfluidic structures may be arranged on or in the rotary body 100. For instance, the rotary body 100 is divided into several fan-shaped regions, and microfluidic structures may be arranged individually on or in each of the divided regions. Particularly, FIG. 1 shows one exemplary divided region of the rotary body 100 where multiple microfluidic structures are formed. The rotary plate 100 has a rotation axis 110 and a circumference or periphery 111.

The microfluidic structures arranged in the rotary body 100 include a plurality of chambers, a plurality of channels that connect the chambers with each other, and a plurality of valves that control a flow of fluid through the channels. The chambers are also in fluid communication with the channels. The microfluidic structures can be provided by two disks that overlap each other to form the disk-shaped rotary body 100 and three-dimensional patterns which define the chambers, channels and valves. Among the two disks, the disk disposed on the top side may be made from a transparent material to allow observations of movements of fluid and reactions. A method of manufacturing such microfluidic structures is already known to those of ordinary skill in the art.

Configuration of the microfluidic structures of the microfluidic device 101 will now be described in detail. Each of the micro fluidic structures includes a sample chamber 11 that contains a fluid sample and a buffer chamber 12 that contains a buffer solution. Although not illustrated, each of the sample chamber 11 and the buffer chamber 12 includes an inlet. A user can introduce a sample and an appropriate buffer solution through the inlet.

A mixing chamber 14 is positioned at a larger distance from the rotation axis 110 than the sample chamber 11 and the buffer chamber 12. Also, the mixing chamber 14 is connected to and in fluid communication with the sample chamber 11 and the buffer chamber through first and second channels 21 and 22, respectively. The first and second channels 21 and 22 include valves 31 and 32, respectively. The valves 31 and 32 control the flow of fluid. The mixing chamber 14 has an outlet at the farthest region from the center (or rotation axis 110) of the rotary body 100, and a valve 34 is placed at the outlet side. That is, the distance from the rotation axis 110 to the inlet of the mixing chamber 14 is smaller than the distance from the rotation axis 110 to the outlet of the mixing chamber 14. The mixing chamber 14 may have a wide top and narrow bottom shape in which its inlet port area has a greater width than the outlet port area. That is, the portion of the mixing chamber 14 close to the valve 34 may have a smaller sectional area than other portions of the mixing chamber 14. Thus, an inner portion of the valve 34 may be formed in a channel. The second channel 22 that connects the buffer chamber 12 with the mixing chamber 14 may be connected to a portion close to the outlet of the mixing chamber 14. The mixing chamber 14 may contain magnetic beads M1 which are previously introduced, and can be supplied with a fluid sample from the sample chamber 11 and a buffer solution from the buffer chamber 12.

A first waste chamber 15 is disposed farther away from the center or rotation axis 110 of the rotary body 100 than the mixing chamber 14. The first waste chamber 15 may be connected with and in fluid communication with the portion of the mixing chamber 14 close to the valve (i.e., the portion of the mixing chamber 14 having the smaller sectional area than other portions) by a third channel 25. An inter-region between the valve 34 and the third channel 25 needs to have a space sufficient for the magnetic beads M1 to be collected. The third channel 25 connected with the waste chamber 15 includes valves 35 and 45 that control fluid flow.

A cell lysis chamber 16 is disposed farther away from the center of the rotary body 100 than the outlet of the mixing chamber 14. An inlet of the cell lysis chamber 16 is connected with the outlet of the mixing chamber 14 through a fourth channel 26. An outlet of the cell lysis chamber 16 may extend toward the center of the rotary body 100. In such a case, due to the centrifugal force, the cell lysis chamber 16 can hold the magnetic beads M1 that flow into the cell lysis chamber 16 through the inlet of the cell lysis chamber 16. The outlet of the cell lysis chamber 16 may be connected with a second waste chamber 17 through a fifth channel 27. The fourth and fifth channels 26 and 27 connected respectively with the inlet and outlet of the cell lysis chamber 16 include valves 46 and 47, respectively. The valves 46 and 47 allow the cell lysis chamber 16 to hold fluid that contains concentrated magnetic beads M1.

Each of the first and second waste chambers 15 and 17 includes an exhaust port 29 that can exhaust a gas when fluid flows into the first and second chambers 15 and 17. Although not shown in FIG. 1, the other chambers may also include the illustrated exhaust ports 29.

The cell lysis chamber 16 holds the magnetic beads M1 which captures a target cell or virus through specific or non-specific couplings. In the cell lysis chamber 16, a laser ablation using a laser beam from outside is performed in order to destruct the captured cell or virus. A laser beam application and heating of magnetic beads makes it possible to attain a rapid cytolysis. The laser supplies radiant energy to heat the cell captured on the magnetic beads and simultaneously gives physical and mechanical shocks to the magnetic beads, so that the captured cell can be destructed.

The above cytolysis using the magnetic beads and laser has the advantage of reducing the number of nucleic acid separation procedures, as the cytolysis using the laser and magnetic beads causes denaturation of proteins of the cell. The denatured proteins and cell residues adhere again to the magnetic beads. Such magnetic beads can be separated from a nucleic acid extraction solution by using a gravitational force, centrifugal force or magnetic force. This can reduce a detection limit of a target cell. The decrease in the number of nucleic acid extraction procedures can shorten a nucleic acid extraction period. Increasing the amplitude of a signal improves a polymerase chain reaction (PCR)-based analysis. A period of time required to denature (dissolve) the cell using the laser and magnetic beads may be approximately 40 seconds.

Laser ablation refers to all phenomena occurring at a material exposed to a laser beam. For example, the laser ablation may rapidly increase a surface temperature of the material up to several hundred to several thousand degrees Celcius. If the surface temperature of the material increases more than the evaporation point of the material, not only will the material in a liquid state be evaporated, but also saturated vapor pressure will rapidly increase at the surface of the material. The saturated vapor pressure is expressed as a function of temperature based on the Clausius-Clapeyron formula. In the case of a high power pulse laser working process, the saturated vapor pressure commonly increases up to several tens of atmospheric pressure. Along with the vapor eruption, pressure that exerts on the surface of the material is called a repelling pressure. Assuming that vapor pressure is 'Psat', the magnitude of the repelling pressure is approximately 0.56 Psat.

A shock wave is generated in a working process using a laser that has a large instantaneous intensity such as a pulse laser. The pressure of vapor produced from the surface of a material that is heated above an evaporation point for a short period of time in a range of several nanoseconds to several tens of nanoseconds increases up to several atmospheric pressures to several tens of atmospheric pressures, and generates a shock wave as the vapor expands to adjacent atmosphere. Vapor expansion due to a high pressure causes the material to be exerted with a pressure of approximately 0.56 Ps, where 'Ps' represents saturated vapor pressure at the surface.

The laser used in the present embodiment may include a pulse laser or a continuous wave (CW) laser. If the laser power is too low, laser ablation may not be performed effectively. For the CW laser, a laser power of approximately 10 mW or more needs to be transferred, and for the pulse laser, a laser power of approximately 1 mJ/pulse or more needs to be transferred. In one embodiment, the pulse laser has a laser power of approximately 3 mJ/pulse or more, and the CW laser has a laser power of approximately 100 mW or more. This laser power range is set because sufficient energy is not often transferred when a laser power of the CW laser is less than approximately 10 mW, and that of the pulse laser is less than approximately 1 mJ/pulse.

The laser should be generated within a specific range of wavelengths that the magnetic beads can absorb. The laser is generated at a wavelength of approximately 400 nm or more. In one embodiment, the laser has a wavelength of approximately 750 nm to 1,300 nm. If the wavelength is less than approximately 400 nm, nucleic acids are likely to be denatured or damaged. Also, the laser may be generated to have more than one range of wavelengths. That is, the laser may have a wavelength within the aforementioned wavelength range, or may have more than two different wavelengths.

The magnetic beads M1 have a surface that allows a specific coupling with a target cell, so that the target cell (including a cell or a virus) can be captured from a biological sample such as whole blood, saliva or urine. The surface of the magnetic beads M1 may have an antibody that has an affinity to the target cell or virus, or with a metal oxide-based material.

Since the antibody can capture selectively a target or desired cell or virus, the antibody can be useful for detecting the cell or virus at a low concentration. Magnetic beads coupled with an antibody that can specifically bind a target cell or virus are manufactured and merchandised by Invitrogen or Qiagen. Exemplary products of the magnetic beads are Dynabeads®, Genomic DNA Blood by Invitrogen, Dynabeads® anti-*E. coli* O157 by Invitrogen, CELLection™ Biotin Binder Kit by Invitrogen, and MagAttract Virus Min M48 Kit by Qiagen.

The magnetic beads coupled with the specific antibody allows separation of various target biological substances which include, but are not limited to, Diphtheria toxin, *Enterococcus faecium, Helicobacter pylori*, HBV, HCV, HIV, Influenza A, Influenza B, *Listeria, Mycoplasma pneumoniae, Pseudomonas* sp., Rubella virus, and Rotavirus. The metal oxide-based material includes $Al_2O_3$, $TiO_2$, $Ta_2O_3$, $Fe_2O_3$, $Fe_3O_4$, or $HfO_2$. The metal oxide-based material includes $Al_2O_3$ or $TiO_2$. In one embodiment, the metal oxide-based material is $Al_2O_3$. The metal oxide-based material may be deposited using a known method such as physical vapor deposition (CVD), atomic layer deposition (ALD) or a sol-gel method.

The magnetic beads M1 each may have a size (diameter) of approximately 50 nm to 1,000 μm. In one embodiment, the magnetic beads M1 may have an average diameter of approximately 1 μm to 50 μm. Also, the magnetic beads M1 may be a mixture of those having different average sizes. That is, the magnetic beads M1 may have substantially the same size or be a mixture of magnetic beads with different sizes.

The magnetic beads M1 may include any material that is magnetic. In particular, the magnetic beads M1 each include at least one selected from a group consisting of strong magnetic metals, including Fe, Ni and Cr, and oxides thereof.

Figure 2:
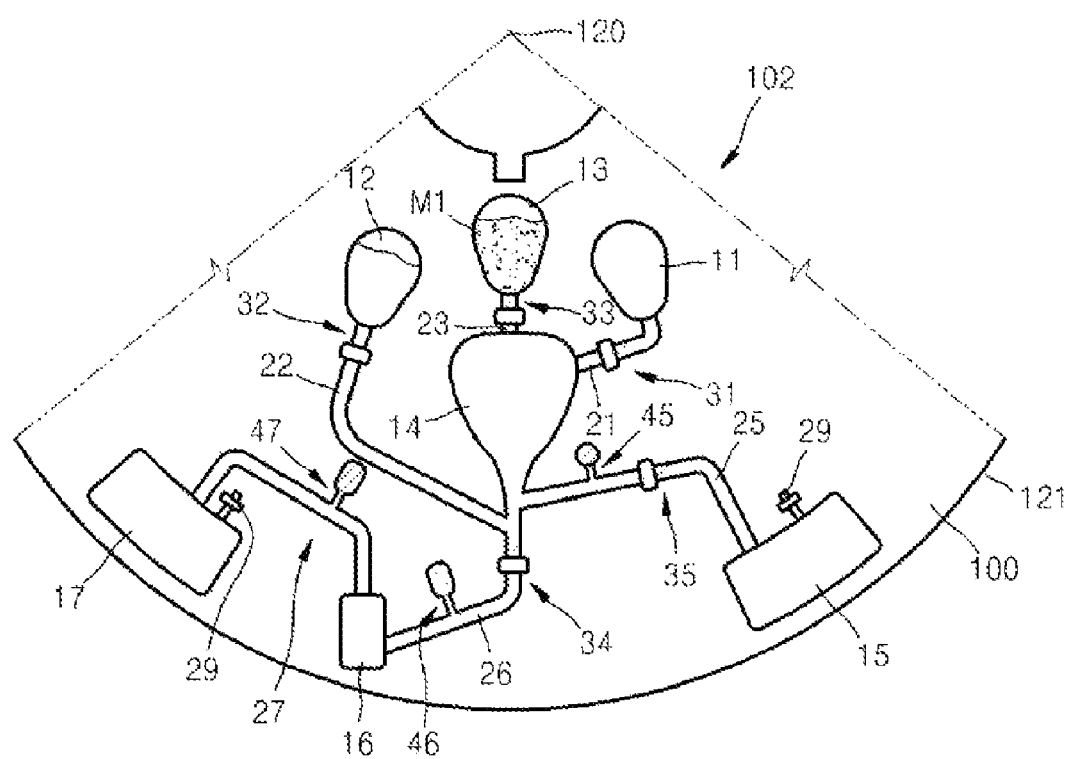
FIG. 2 illustrates a simplified top view of a microfluidic device for extracting nucleic acids according to a second embodiment of the present invention.

FIG. 2 illustrates a simplified top view of a microfluidic device for extracting nucleic acids according to a second embodiment of the present invention. The configuration of the microfluidic device 102 is substantially the same as the microfluidic device 101 illustrated in FIG. 1. The difference is that a magnetic bead chamber 13 that contains the magnetic beads M1 is disposed in a proximity to the center of the rotary body 100. The difference from the center (or rotation axis 120) of the rotary body 102 to the magnetic bead chamber 13 is shorter than the distance from the rotation axis 120 to the mixing chamber 14. Another difference is that the magnetic beads M1 are provided to the mixing chamber 14 by opening a valve 33 provided at a channel 23 which connects the magnetic bead chamber 13 with the mixing chamber 14. The magnetic bead chamber 13 is in fluid communication with the mixing chamber 14. The magnetic beads M1 are introduced into the chamber 13 as a dispersion in a solvent or a liquid carrier.

Figure 3A:
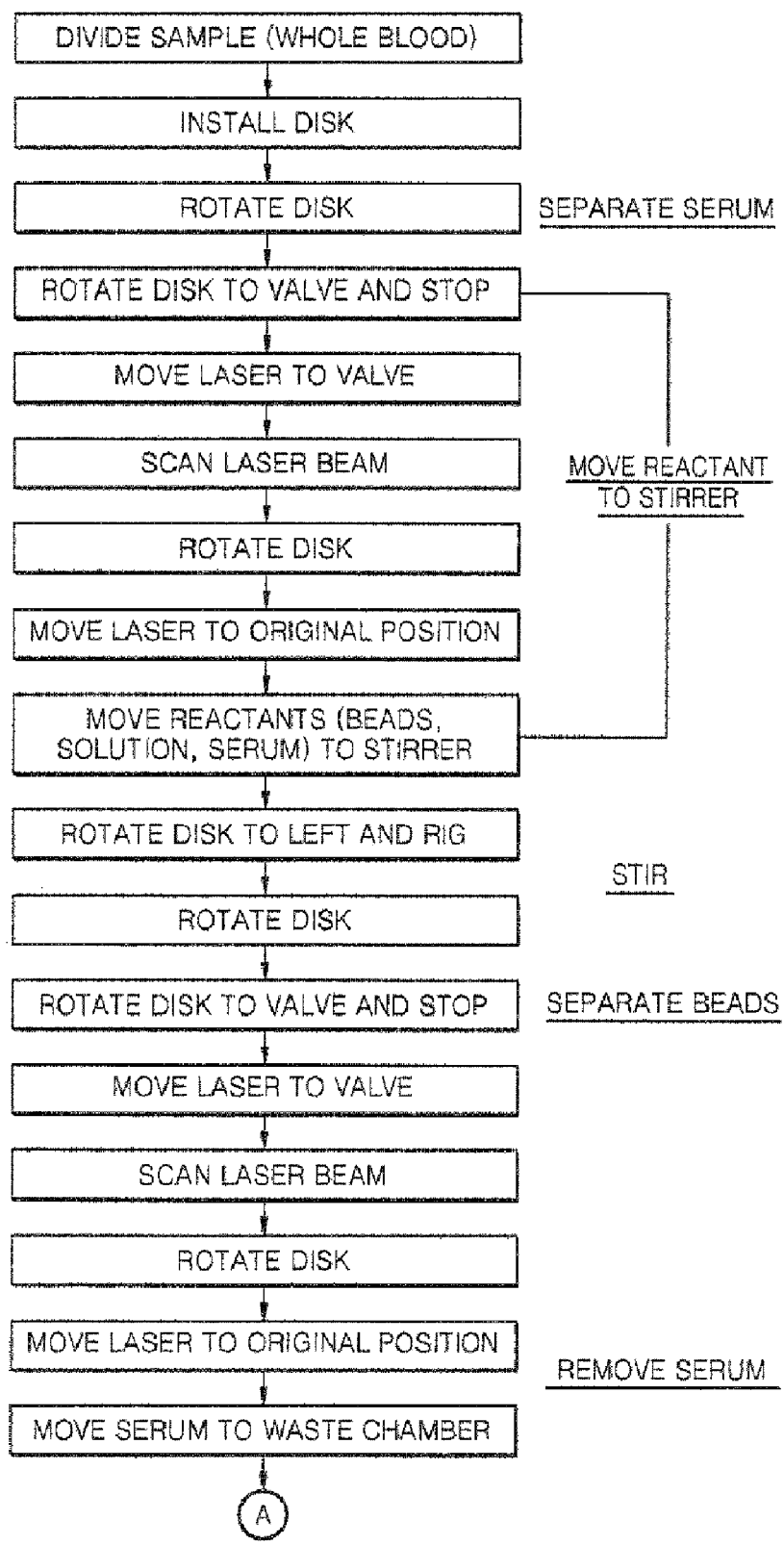
FIGS. 3A through 3C are flowcharts for describing nucleic acid extraction procedures using a microfluidic system according to an embodiment of the present invention.
Figure 3B:
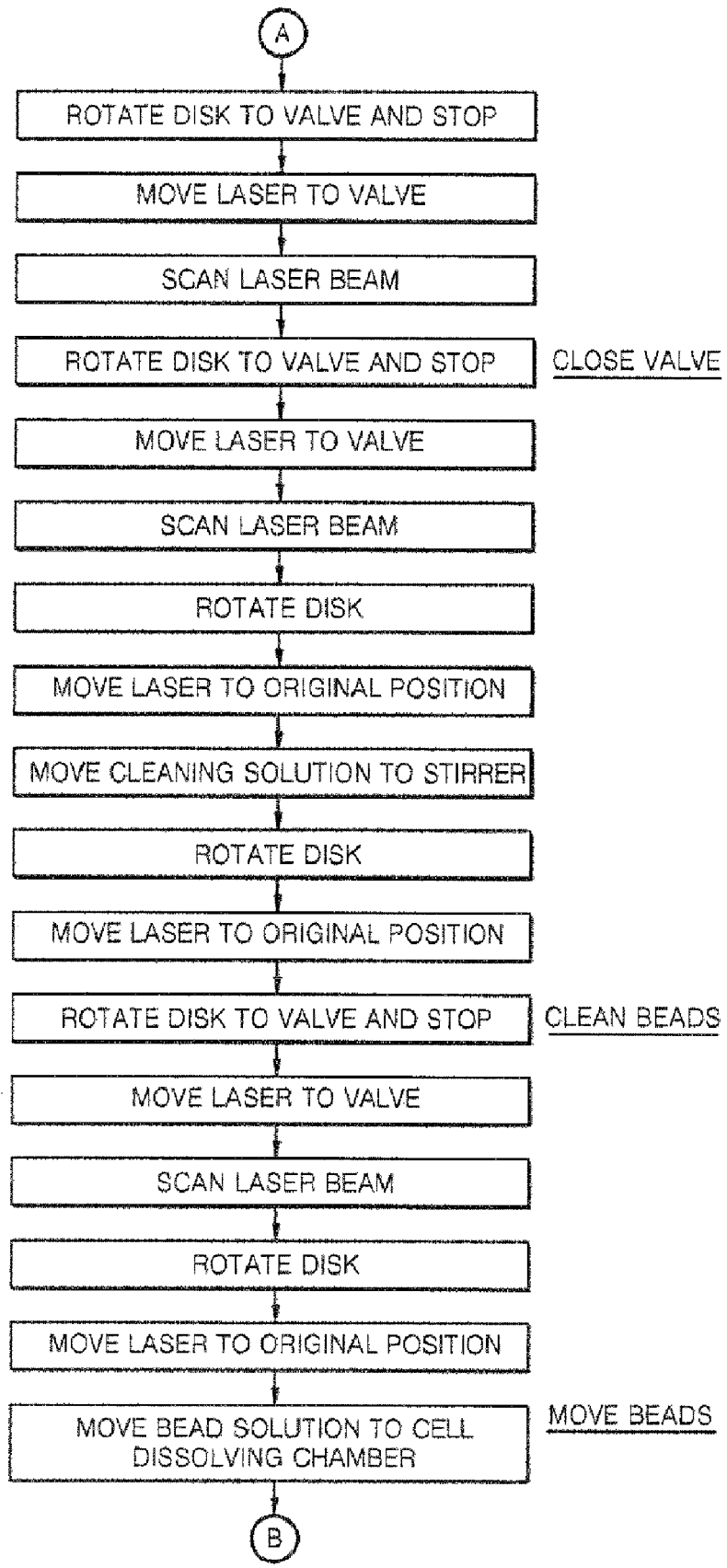
Figure 3C:
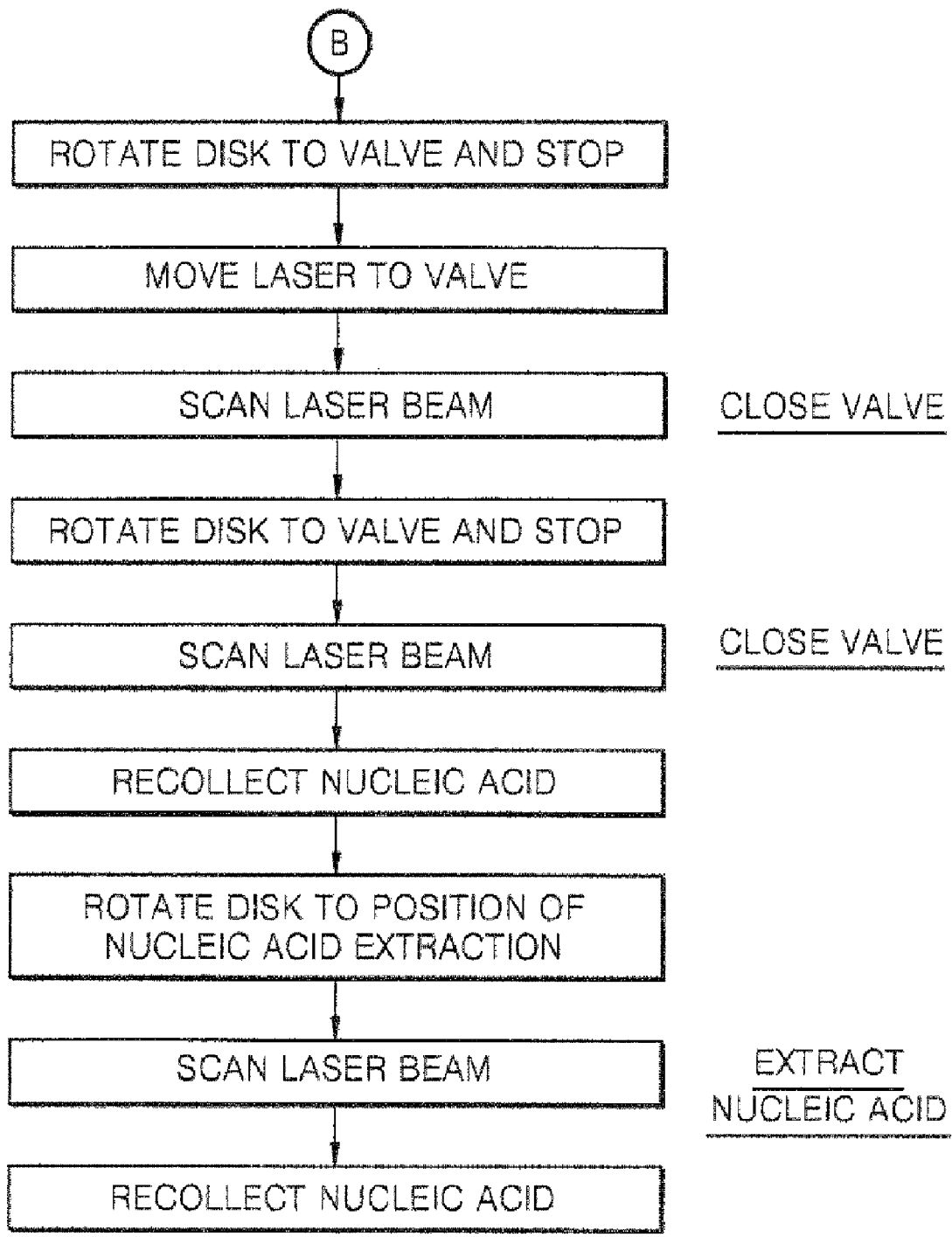

FIGS. 3A through 3C are flowcharts for describing nucleic acid extraction procedures using a microfluidic system according to an embodiment of the present invention.

Referring to FIGS. 1 and 3A, a portion of a blood sample is put into the sample chamber 11, and placed on a disk. The rotary body is rotated in order to separate serum from the blood sample. The disk is rotated in a direction which allows the valve 31 may be positioned close to a laser beam source (not shown). As the disk rotates or once the valve 31 is positioned, a laser beam source (not shown), which does not rotate, but moves along a radius direction of the rotary body at a fixed track, is moved toward the position where the valve 31 is now positioned, and a laser beam is applied to the valve 31. Upon the laser beam application, the valve opens the first channel 21 and the serum separated from the sample chamber 11 flows into the mixing chamber 14, where the serum is mixed with the magnetic beads M. The disk is rotated to the right and left to stir the serum and the magnetic beads M1. The disk is moved to the valve 35 and stopped at that position, and a laser is moved to that position in order to scan a laser beam over the valve 35. Upon application of the laser beam, the valve melts, resulting in opening of the channel 25, and the serum is moved to the waste chamber 15 by spin of the disk.

Referring to FIGS. 1 and 3B, the disk is rotated toward the valve 45 and stopped, and a laser beam scans over the valve 45. The laser beam application will cause a melting and expansion of valve into the channel, resulting the valve 45 being closed.

The disk is rotated to the valve 32, and a laser beam scans over the valve 32 so as to cause the valve 32 open and a washing solution to move from the buffer chamber 12 to the mixing chamber 14. The disk is rotated in order to wash the magnetic beads M1. The disk is rotated toward the valve 34, and a laser beam is scanned over the valve 34 so as to cause the valve 34 open and a solution containing the magnetic beads M1 to move to the cell lysis chamber 16.

Referring to FIGS. 1 and 3C, the disk is rotated in a direction that allows the valve 46 moves to a location where it overlaps or is in proximity with a laser beam source, and a laser beam scans over the valve 46 in order to close the valve 46. Subsequently, a laser beam scans over the valve 47. Valve 47 is then closed, and nucleic acid solution is recollected. The disk is rotated in a way that allows an nucleic acid extraction unit to be moved close to a laser and a laser beam is applied to the extraction unit, thereby nucleic acids are extracted.

Figure 4A:
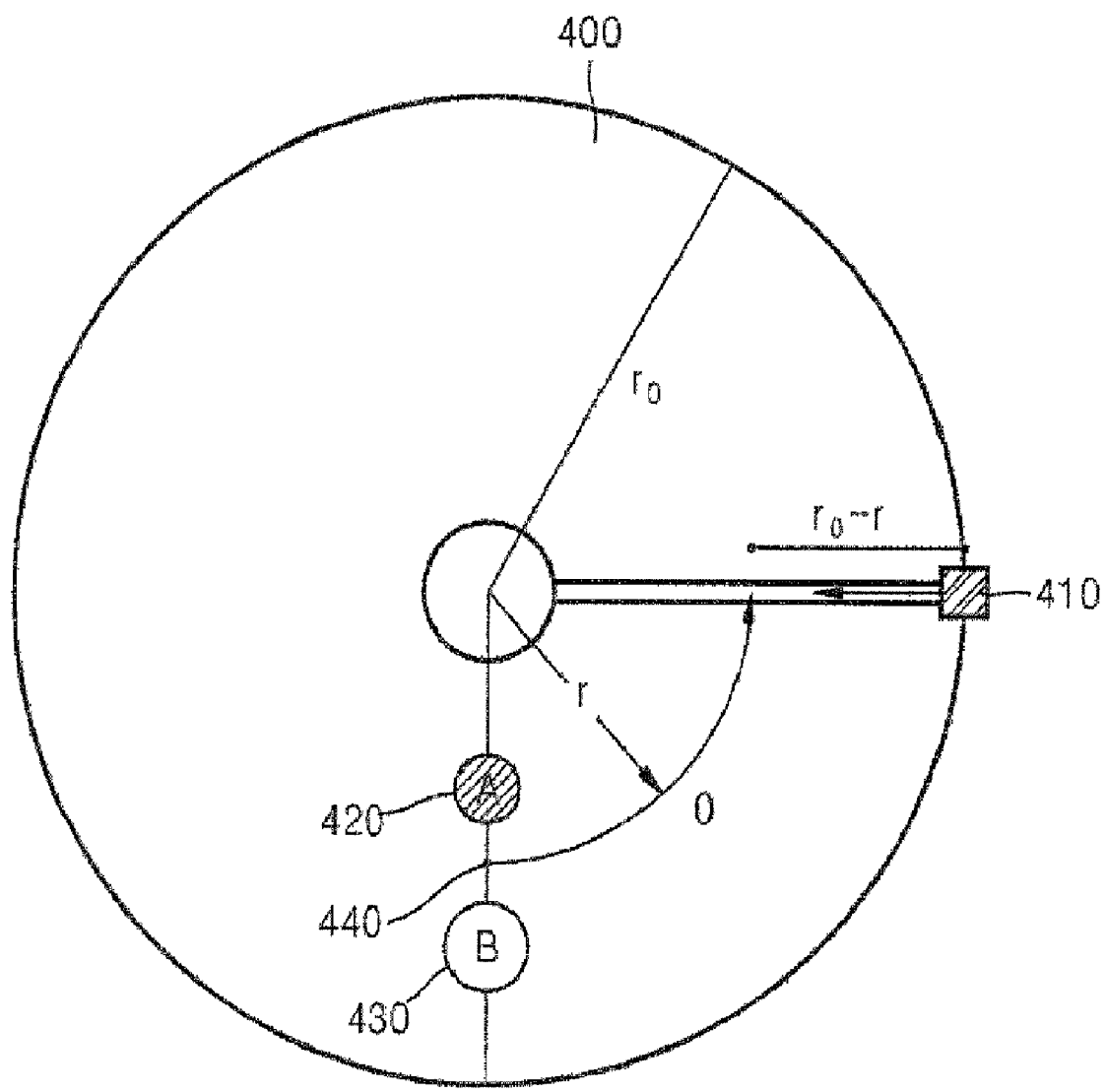
FIGS. 4A through 4C are diagrams for describing a control of operations of valves of a microfluidic structure according to an embodiment of the present invention.
Figure 4B:
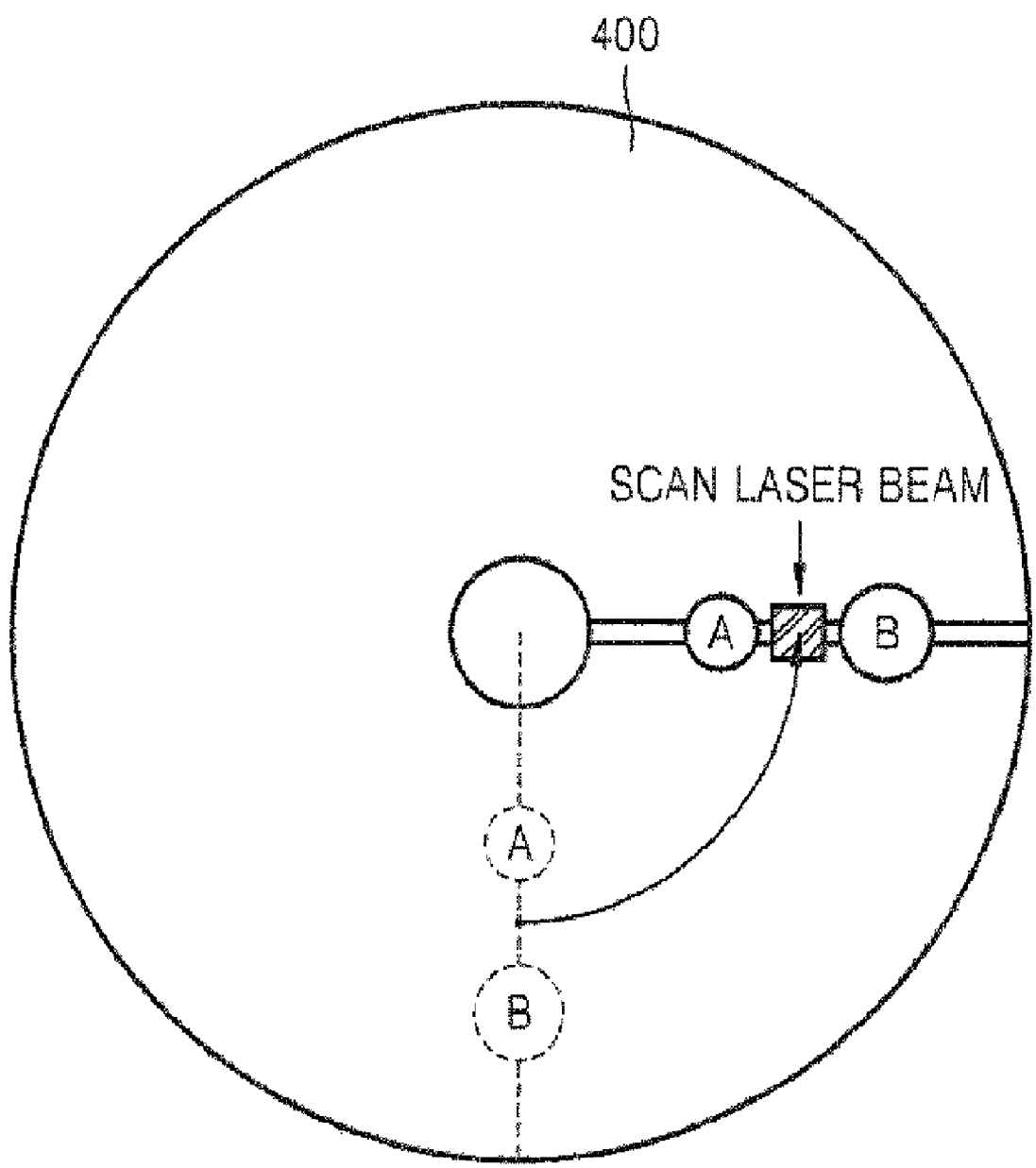
Figure 4C:
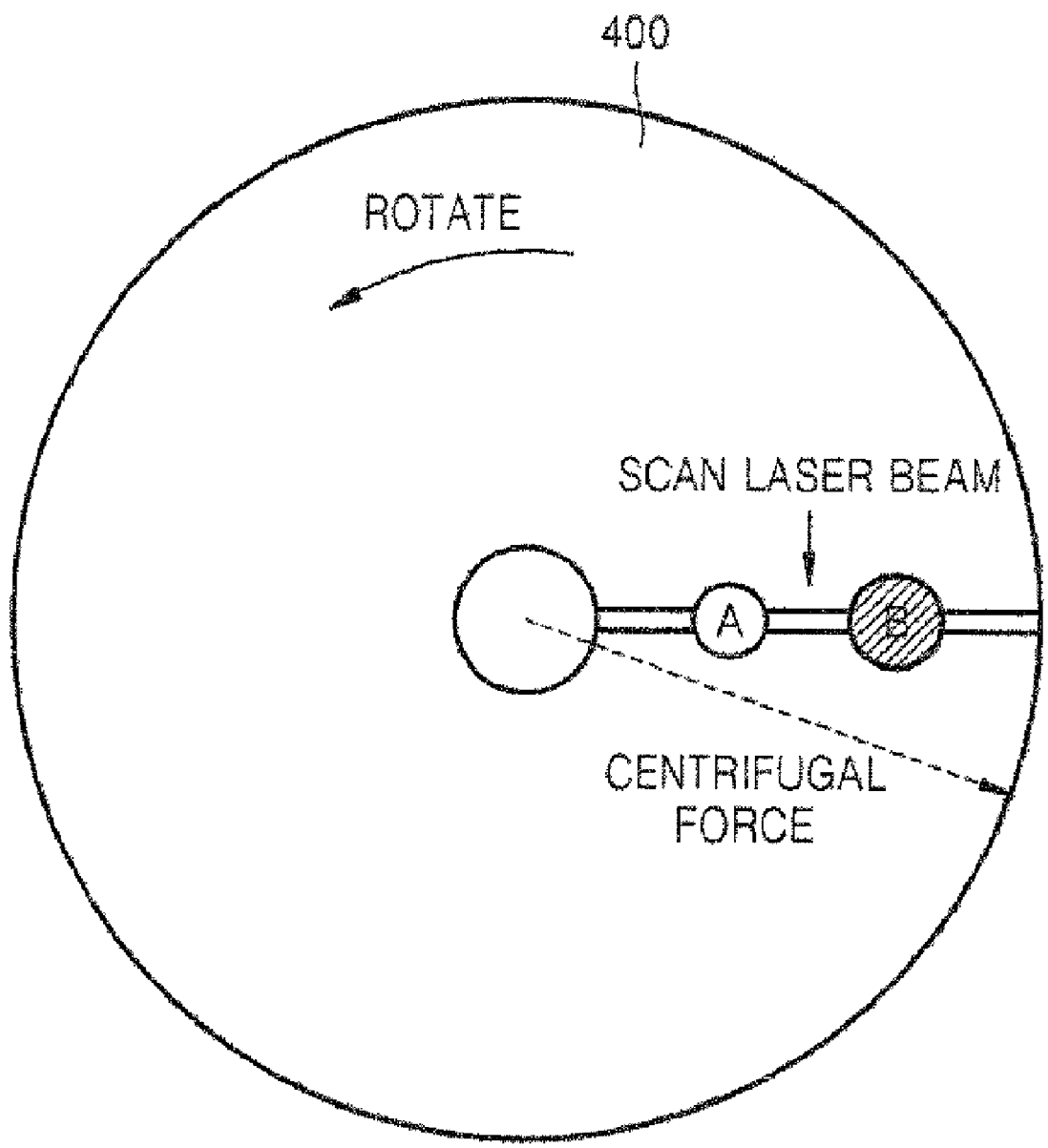

FIGS. 4A through 4C are diagrams for describing a controlled operation of valves of a microfluidic structure according to an embodiment of the present invention.

Referring to FIG. 4A, a disk-shaped rotary body 400, a radiation energy source 410 a reactor A 420, a reactor B 430, and a valve 440 are illustrated. The reactor A 420 contains a fluid sample, and the reactor B is empty. The reactors A 420 and B 430 are in fluid communication with each other through a channel. The valve 440 is positioned in the middle of the channel. The radiation energy source 410 is placed in a manner so as to move forward and backward along a radius of the rotary body 400. The radiation energy source 410 is installed in such a way that it does not rotate together with the rotary body 400. The rotary body 400 has a radius $r_0$, and the valve 440 is positioned a distance away from the center of the rotary body 400 by a value of 'r'. The valve 440 and the radiation energy source 410 are separated apart from each other by an angle of 'θ'. In order to control an operation of the valve 440 placed at a specific position (r, θ) of the rotary body 400, the rotary body 400 is rotated by 'θ' in a counterclockwise direction (i.e., valve 440 moves towards the radiation energy source) and the radiation energy source 410 moves to the center of the rotary body 400 in the radius direction by '$r_0$-r'.

Referring to FIG. 4B, the radiation energy source 410 is positioned where the valve 400 is placed at a specific position (r, θ) of the rotary body 400. As illustrated, the radiation energy source 410 applies radiation energy over a predetermined region of the valve 440. A laser is exemplified in the present embodiment as the radiation energy source 410. However, light emitting devices or xenon lamps may be used as the radiation energy source 410. Also, a plurality of radiation energy sources may be used. When a laser is used as the radiation energy source, the laser may include at least one laser diode. A laser beam emitted from the laser has a wavelength of approximately 400 nm to 1,300 nm. In one embodiment, a laser with a power of approximately 1.5 W, which emits an electromagnetic wave of a wavelength of approximately 808 nm, is used. The laser beam activates heat generating particles, which are present in the valve region, to emit heat and be melted, causing the valve 400 open. When the valve 400 is open, a fluid may freely move from the reactor A 420 to the reactor B 430.

Referring to FIG. 4C, when the rotary body 400 rotates while the valve 400 is open, the fluid sample contained within the reactor A 420 moves to the reactor B 430 by the action of the centrifugal force generated by the rotation of the rotary body 400.

By repeating the above controlled operation described in FIGS. 4A through 4C, it is possible to operate a plurality of valves placed at different positions in a sequential order in a batch mode. Although the operation of an open valve is explained above, a closed valve which closes a channel upon the action of a radiation energy may be operated in a similar manner.

Figure 5:
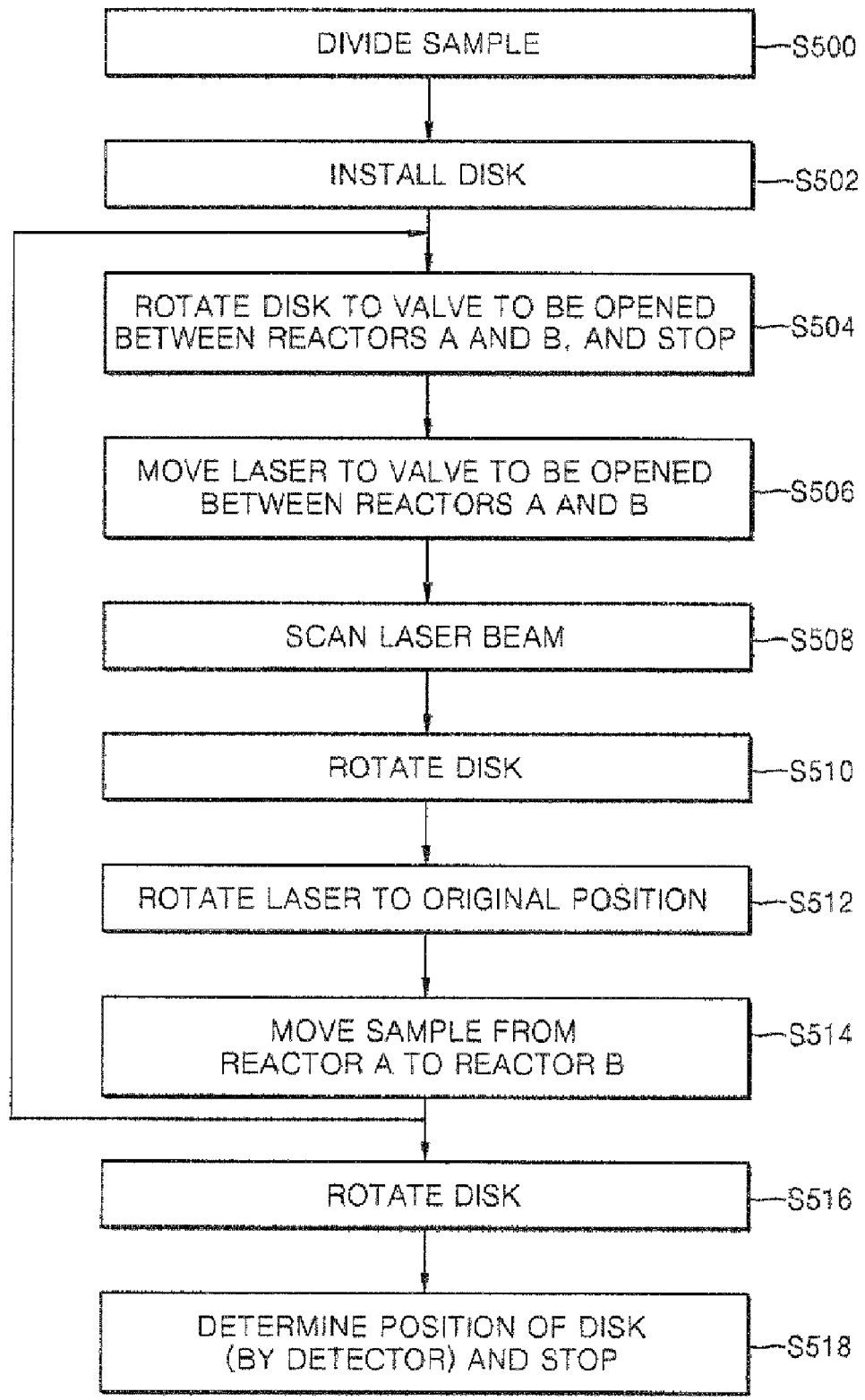
FIG. 5 is a flowchart for describing the control of the operations of a valve illustrated in FIGS. 4A through 4C.

FIG. 5 is a flowchart for describing the controlled operation of the valve 440 illustrated in FIGS. 4A through 4C.

In operation S500, a sample is put into the reactor A of the microfluidic structure. In operation S502, a disk is installed within the microfluidic system. In operation S504, the disk is rotated by a certain angle (e.g., Θ in FIGS. 4A-4C) so that the valve 400 moves to a position where it is applied with an energy thereby opening a channel between the reactor A and the reactor B. In one embodiment, the energy is a laser beam.

In operations S506 and S508, the laser is moved to the location where the valve 440 is positioned and applies a laser beam to the valve 440. The operations S506 and S508 may be performed simultaneously. In operation S510, as the valve 440 is open by the heat that is generated by the laser beam. The disk is rotated in a reversed direction to be moved back to the original position, in operation S512. In operation S514, when the disk is rotated, the fluid sample moves from the reactor A to the reactor B. A physical and mechanical reaction of the fluid sample is repeated by repeatedly performing the above sequence of operations S504 to S514. In operation S516, the disk is rotated. In operation S518, the obtained target substance is transferred to and analyzed at a detection unit (not shown).

FIG. 6 is a flowchart for describing a method of automatically detecting a position where a laser beam is applied. In the present embodiment, a valve comprises a heat generating substance. An example of the heat generating substance include, but is not limited to, a ferrowax. Ferrowax is composed of ferrofluid and paraffin wax. Ferrofluid may be made up of a magnetic iron nanoparticles and surfactant. Magnetic iron nanoparticles may be iron oxide nanoparticles. Ferrowax, in which paraffin wax is embedded with iron oxide nanoparticles, melts relatively weak intensity of laser irradiation. In operation S600, a tag material or marker is added. In one embodiment, a fluorescence tag material such as cy3 is added to the ferrowax. This exemplary material, cy3, emits an electromagnetic wave having a wavelength of approximately 570 nm when the cy3 absorbs an electromagnetic wave of a wavelength of approximately 550 nm. In operation S602, a radiation energy source such as a laser diode scans an electromagnetic wave having a specific wavelength over the cy3-containing valve. The fluorescent tag material that absorbs the electromagnetic wave of the certain wavelength emits an electromagnetic wave of another certain wavelength. In operation S604, an optic detection module is used to scan the valve. The optic detection module can sense the valve that emits an electromagnetic wave having a specific wavelength and pinpoints the position of the valve over the disk in specific coordinates such as (r, θ) and (x, y). Detecting and identifying the position of a target valve in specific coordinates allows an effective control of valve operations. The automatic detection and identification of a position of an unit in a microfluidic system may be applied to other parts of microfluidic apparatuses that need a controlled positioning.

FIG. 7 illustrates a block diagram of an apparatus for controlling a microfluidic system according to an embodiment of the present invention.

The apparatus includes a central control block 700, a rotator control block 710, a position control block 720, a radiation energy source control block 730, a detector control block 740, a communication device 750, and a storage device 760.

The central control block 700 controls the overall operation of the microfluidic system. That is, the central control block 700 controls the rotator control block 710, the position control block 720, the radiation energy source control block 730, the detector control block 740, the communication device 750, and the storage device 760. For instance, the central block 700 operates using a frequency of approximately 20 MHz and may include miniaturized microcomputers with a capacity of approximately 5 MIP. Also, the central control block 700 receives sample analysis information obtained by the detector and information necessary for position control within the microfluidic system, and performs an operation to compute the coordinates of the position.

The communication device 750 can perform data communications with external processing devices. For example, the communication device 750 converts a digital signal having a voltage of approximately 0.5 V to a standard RS232 signal having a voltage of approximately ±15V, and transfers the standard RS232 signal to a RS232 port. The storage device 360 stores variables and data necessary for the microfluidic system to analyze a fluid sample, and provides the appropriate variables or data through the central control block 700 when necessary. For example, the storage device 760 may use a 64 kbit (8 KB)-level electrically erasable programmable read-only memory (EEPROM).

The rotator control block 710 rotates a rotary body in response to a control signal from the central control block 700, and controls the rotator that makes the fluid sample flow using the centrifugal force generated by the rotation of the rotator. In response to a control signal from the central control block 700, the position control block 720 controls the position of a moving unit that moves to a target position of the microfluidic structure. In response to a control signal from the central control block 700, the radiation energy source control block 730 controls the energy of the radiation energy source that scans an electromagnetic wave over the target position of the microfluidic structure. The detector control block 740 controls a signal that is detected by the detector so as to be output to the central control block 700. The detector detects optical information related to reactions of the fluid sample and wavelength information of waves emitted from certain positions in the microfluidic apparatus. The configuration and control operation of the individual control blocks illustrated in FIG. 7 will be described with reference to FIGS. 8 through 11.

Figure 8:
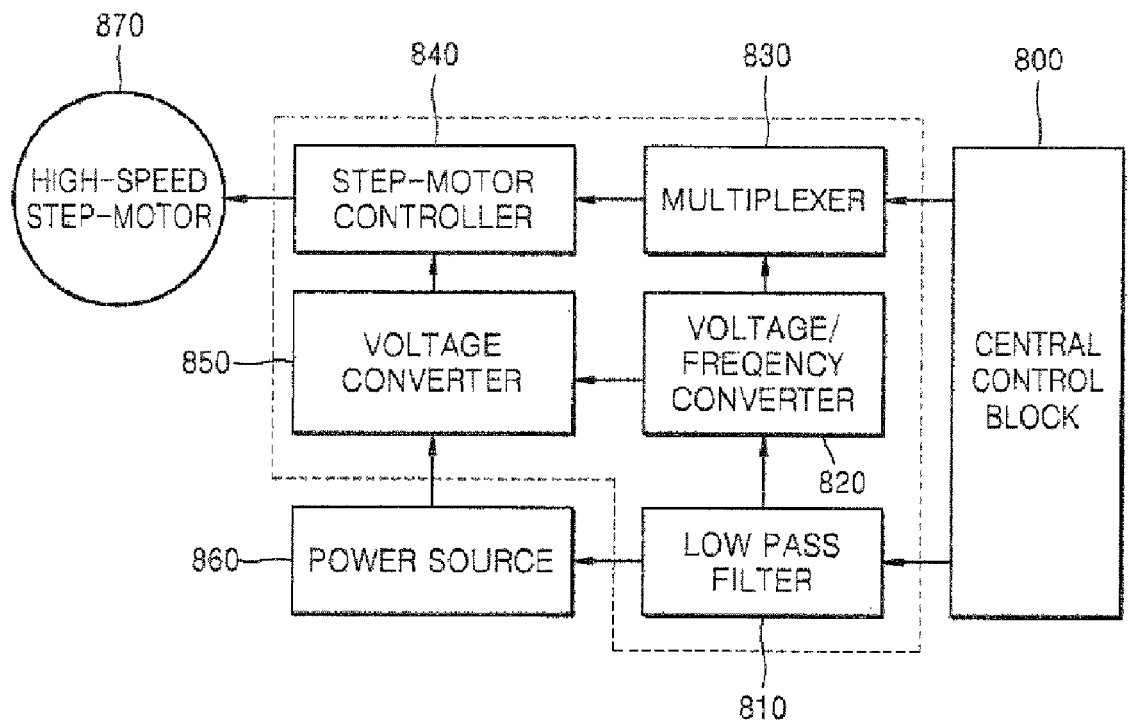
FIG. 8 illustrates a block diagram of the rotator control block illustrated in FIG. 7.

FIG. 8 illustrates a block diagram of the rotator control block illustrated in FIG. 7.

A central control block 800, the rotator control block marked with a dotted line, a voltage converter 850, a power source 860, and a rotator 870 are illustrated.

The rotator control block includes a low pass filter 810, a voltage/frequency converter 820, a multiplexer 830, and a step-motor controller 840. Although a step-motor is exemplified as the rotator 870 in the present embodiment, other devices can be used instead. Control operation of the step-motor will now be described.

The low pass filter 810 receives a voltage signal whose pulse width is modulated by the central control block 800. The low pass filter 810 removes a frequency signal having a frequency greater than approximately 1 Hz and outputs the resultant signal to the voltage/frequency converter 820. The low pass filter 810 is used to convert a pulse signal into an analog signal. A secondary filter configured in a combination of a resistor and a capacitor is one example of the low pass filter 810. The voltage/frequency converter 820 converts a voltage of the analog signal input from the low pass filter 810 into a frequency pulse, and is used to continuously increase the frequency for high-speed rotation. The multiplexer 830 multiplexes the frequency-converted signal input from the voltage/frequency converter 820 and outputs the multiplexed signal to the step-motor controller 840. The step-motor controller 840 uses a driving voltage that is converted from a main power having a voltage level of approximately 7.2 V, which is provided from the power source 880, into a high voltage level of approximately 24 V at the voltage converter 850. The step-motor controller 840 includes a field effect transistor (FET) driver and micro-step tables (1/1 to 1/8), and thus, the step-motor controller 840 can be applied to the manufacture of miniaturized devices. Also, the step-motor controller 840 controls the exact position of the step-motor using a step pulse signal input from the central control block 800, and also controls the high-speed rotation of the step-motor using the frequency-converted signal obtained from the low pass filter 810 and the voltage/frequency converter 820 in sequential order. The rotator 870 (e.g., the step-motor) is preferably a high-speed step-motor. The rotator 870 can control the exact position of a target, has an angular resolution of approximately 1.8°, and can rotate at high speed (e.g., approximately 4,000 RPM).

Figure 9:
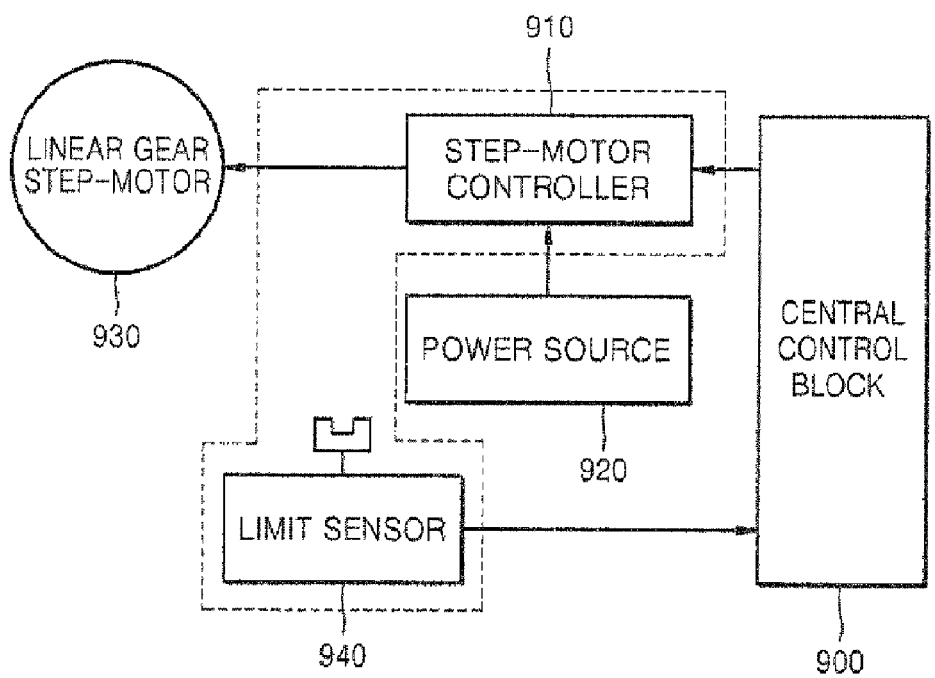
FIG. 9 illustrates a block diagram of the position control block illustrated in FIG. 7.

FIG. 9 illustrates a block diagram of the position control block illustrated in FIG. 7.

A central control block 900, the position control block marked with a dotted line, a power source 920, and a linear gear step-motor 930 are illustrated. The position control block includes a step motor controller 910 and a limit sensor 940. The linear gear step-motor is illustrated as an example of the moving unit 870 in the present embodiment, and this linear gear step-motor is for exemplary purposes only. Operation of controlling the rotation of the linear gear step-motor will now be described.

The step-motor controller 910 receives a pulse signal from the central control block 900, and is supplied with a motor driving voltage of approximately 7.2V from the power source 920 in order to control the linear gear step-motor 930. As with the step-motor controller 840 illustrated in FIG. 8, the step-motor controller 910 includes a field effect transistor (FET) driver and micro-step tables (1/1 to 1/8), and thus, the step-motor controller 840 can be applied to the manufacture of miniaturized devices. The limit sensor 940 senses an electromagnetic wave having a specific wavelength emitted from the moving unit and generates a limit signal that limits the pulse signal, which is output to the central control block 900. The limit sensor 940 makes use of optical interruption. For example, the limit sensor 940 may be configured in a combination of an ultraviolet (UV) light emitting diode (LED) and a photo-transistor. The limit sensor 940 operates when shielded from light. The central control block 900 outputs a position control signal of the moving unit based on the limit signal. The linear gear step-motor 930 is used to detect a magnet that generates a magnetic force in the microfluidic device, a radiation energy source that scans by using an electromagnetic wave, and a specific reaction of a fluid sample, and is also used to move the detector, which detects a specific wavelength, vertically or horizontally in the direction of a radius of the microfluidic device.

Figure 10:
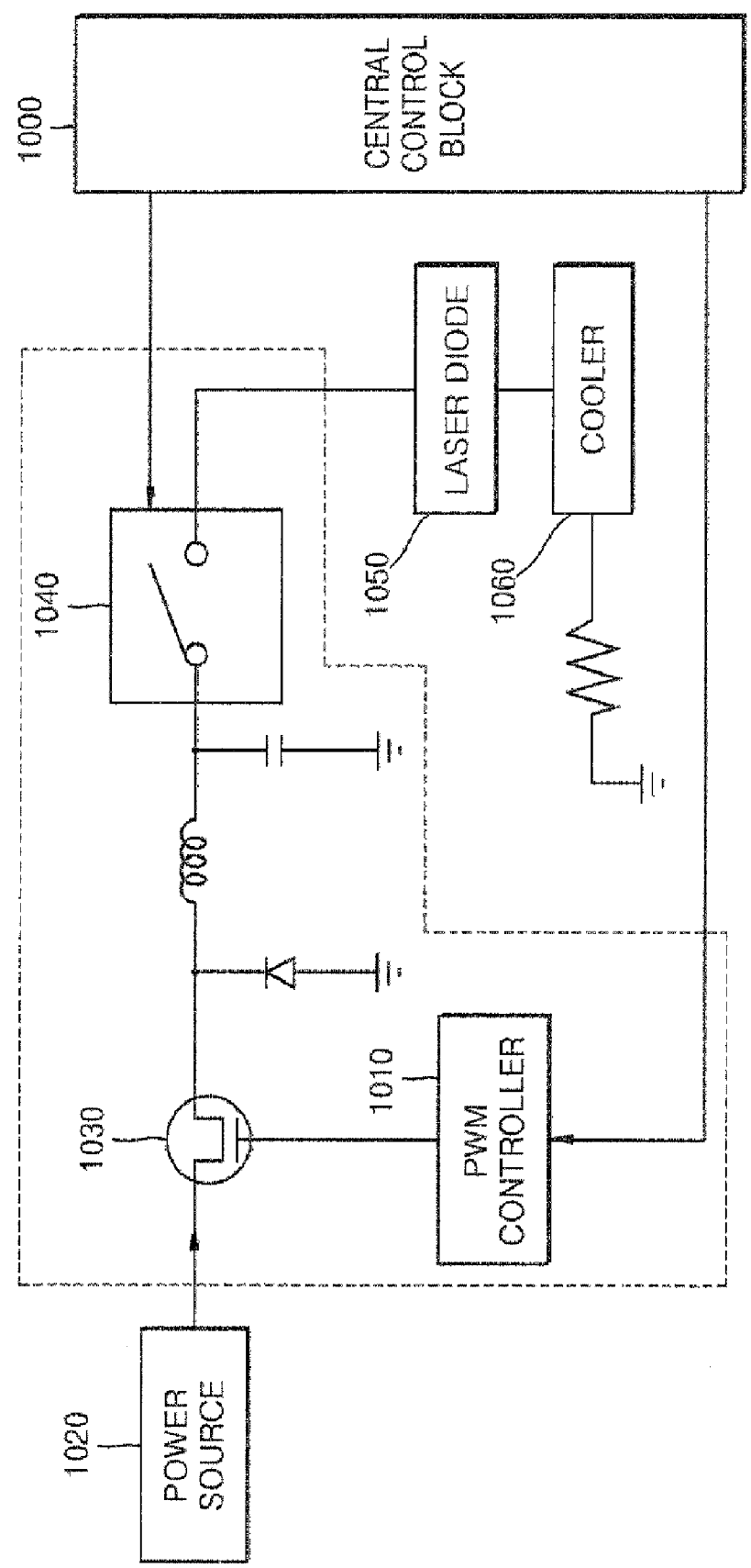
FIG. 10 illustrates a block diagram of the radiation energy source controller illustrated in FIG. 7.

FIG. 10 illustrates a block diagram of the radiation energy source controller illustrated in FIG. 7.

A central control block 1000, the radiation energy source control block marked with a dotted line, a radiation energy source 1050, a cooler 1060, and a power source 1020 are illustrated. In the present embodiment, a laser diode is used as the radiation energy source 1050, but the laser diode is for exemplary purposes only. Thus, light emitting devices and xenon lamps can also be used as the radiation energy source. In one embodiment, the laser diode can scan using an electromagnetic wave of a wavelength of approximately 400 nm to 1,300 nm, and emits UV rays having a wavelength of approximately 808 nm and energy of approximately 2 W.

The radiation energy source control block includes a pulse width modulation (PWM) controller 1010, a switch 1030, a delay switch 1040, and passive devices including a diode, a capacitor and an inductor. The switch 1030 may comprise a P-type channel metal oxide semiconductor field effect transistor (MOSFET). The PWM controller 1010 receives a reference signal from the central control block 1000 and compares the reference signal with an input signal that is input from the power source 1020 and switched. On the basis of the comparison result, the PWM controller 1010 adjusts a duty ratio of a PWM pulse. The diode may include a fast recovery diode that helps the input signal to have a fast current recovery characteristic. The inductor that is connected in parallel with the capacitor stores the pulse-type voltage signal, and outputs the stored signal when the voltage is not applied. That is, the inductor allows a consistent level of current to flow through the laser diode 1050. The delay switch 1040 receives a delay signal from the central control block 1000 and then provides a current signal from outside or cuts off the current in order to protect the laser diode 1050 against undesired signals. The cooler 1060 connected to the laser diode 1050 functions as a heat pump that transfers heat generated at the laser diode 1050 to an external heat sink. Also, the cooler 1060 prevents a decrease in output of the laser diode 1050.

Figure 11:
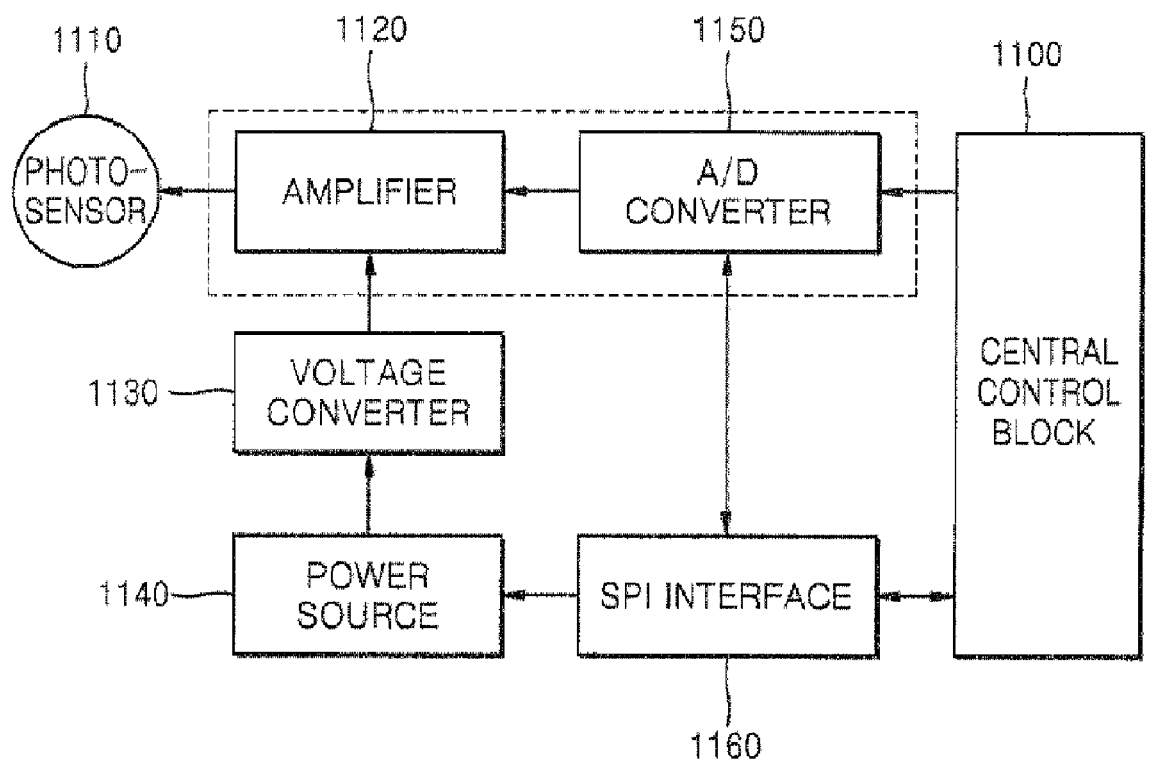
FIG. 11 illustrates a block diagram of the detector control block illustrated in FIG. 7.

FIG. 11 illustrates a block diagram of the detector control block illustrated in FIG. 7.

A central control block 1100, a photo-sensor 1110, the detector control block marked with a dotted line, a power source 1140, and a voltage converter 1130 are illustrated. Although the photo-sensor 1110 is illustrated as an example of the light detector, another device such as a charge coupled device (CCD), a photomultiplier tube or a camera may also be used as the light detector. The photo-sensor 1110 includes a photodiode and a pre-processing amplifier and has an amplitude of approximately $10^9$ V/A.

The detector control block includes an amplifier 1120 and an analog-to-digital (A/D) converter 1150. The amplifier 1120 is a precise OP-AMP and amplifies a signal from the photodiode approximately 100-fold. Particularly, the amplifier 1120 is a differential amplifier that generates and transfers (+) and (−) signals. Thus, the amplifier 1120 can reduce noise, which is often problematic for long-distance precise signal transmission. The amplifier 1120 converts a voltage of approximately 7.2 V provided from the power source 1140 into a voltage of approximately ±15 V at the voltage converter 1130 and uses the converted voltage as a driving voltage. The A/D converter 1150 converts a voltage signal detected by the photo-sensor 1110 into a digital signal so as to be easily manipulated by a user. That is, the A/D converter 1150 allows communication through a peripheral interface 1160 (e.g., a program specific information (PSI) interface). The detection signal converted into the digital signal is output to the central control block 1100 so as to be used in analyzing optical reactions of the fluid sample of the microfluidic system and computing the position of a target valve.

Figure 12:
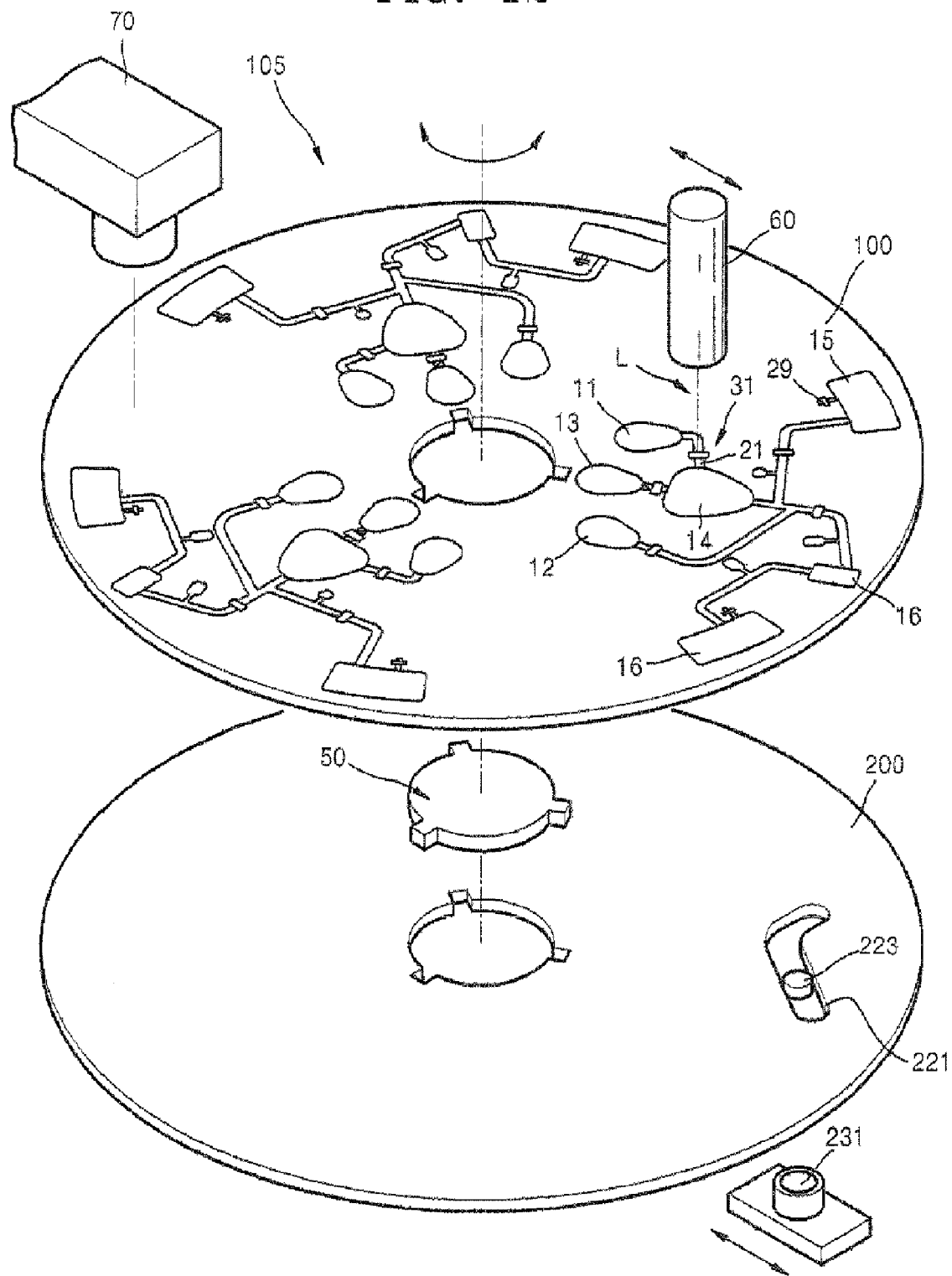
FIG. 12 illustrates a simplified perspective view of a microfluidic system according to a third embodiment of the present invention.

FIG. 12 illustrates a simplified perspective view of a microfluidic system according to a third embodiment of the present invention.

The microfluidic system 105 is arranged on the rotary body 100, and includes the microfluidic device described in the above embodiments, a rotator 50, and a radiation energy source 60. The rotator 50 rotates the rotary body 100, and the radiation energy source 60 scans a laser beam over a predetermined region of the rotary body 100. The microfluidic system 105 may further include a detector 70 that can optically detect intermediate products or final products of reactions taking place in the microfluidic device.

The radiation energy source 60 includes a laser that can be used in the aforementioned laser ablation and includes at least one laser diode. Any laser that can satisfy the above described conditions of output power and wavelengths can be used as the radiation energy source 60. In the case of using a phase-transforming valve which includes heat generating particles, including magnetic beads, the radiation energy source 60 can be used to operate the phase-transforming valve and scan using a radiation energy source to automatically search for the valve position.

Although not illustrated, the microfluidic system 105 may further include a laser adjuster that adjusts the position or direction of the laser 60 in order to allow a scanning laser beam to reach an intended region of the rotary body 100, such as a plurality of phase-transforming valves or a selected region of the cell lysis chamber.

The rotator 50 of the microfluidic system 105 drives the rotary body 100. The rotator 50 is a part of a device that locks with the rotary body 100 and transfers rotation force. Although not illustrated, the microfluidic system 105 may further include a motor that can rotate the rotary body 100 clockwise and counter-clockwise and parts related to the motor.

The microfluidic system 105 includes various control devices as described in the above embodiments with reference to FIGS. 7 through 12.

According to various embodiments of the present invention, a microfluidic system including a microfluidic device can provide DNA that can perform PCR simply by a single manual application of injecting a sample (e.g., a biological sample) into the microfluidic device. The injection of the sample to the microfluidic device triggers serial procedures that are carried out for a short period of time within a microfluidic structure, including a separation of a target cell from the biological sample and concentration and lysis of the separated cell (i.e., cytolysis). Therefore, compared to the conventional DNA extraction which usually requires skilled manipulations and involves complex processes, the DNA extraction according to the embodiments of the present invention can be simplified, thereby saving time and effort. Also, DNA of a target cell can be extracted from a trace amount of the sample. Furthermore, a miniaturized portable microfluidic system can be effectively controlled using the device and method of controlling the microfluidic system.

The above described device and method of controlling a microfluidic system and the microfluidic system according to the present invention can be embodied as a program and stored on a computer readable recording medium. The computer readable recording medium is any data storage device that can store data which can be thereafter read by the computer system. The computer readable recording medium includes a read-only memory (ROM), a random-access memory (RAM), a CD-ROM, a floppy disk, a hard disk, an optical magnetic disk, and carrier waves such as data transmission through the Internet.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for controlling a microfluidic system, wherein the microfluidic system comprises a microfluidic device in which a microfluidic structure is arranged on a rotary body; a rotator which rotates the rotary body; a moving unit which moves from a first position to a second position of the microfluidic device; and an energy source; the apparatus comprising:

a central control block which controls operation of the microfluidic system;

a rotator control block which controls the rotator in response to a first control signal from the central control block, a position control block which controls a position of the moving unit in response to a second control signal from the central control block;

an energy source control block which controls an emission of energy from the energy source in response to a third control signal from the central control block, wherein the energy source emits an electromagnetic wave, and a detector control block which controls a transmission of a detection signal from a detector to the central control block, wherein the detector detects optical information related to a reaction of a fluid sample in the microfluidic structure and wavelength information related to a wave emitted from the microfluidic structure, wherein the moving unit moves the energy source from the first position to the second position in the direction of a radius of the microfluidic apparatus, and wherein the position control block controls the positions of the moving unit moving in the direction of a radius of the microfluidic apparatus, the moving unit moving a magnet, the energy source, and the detector.

2. The apparatus of claim 1, wherein the rotator control block comprises:
  a low pass filter which receives a voltage signal, whose pulse width is modulated, from the central control block and removes a signal having a predetermined frequency or a frequency higher than the predetermined frequency;
  a voltage/frequency converter which converts the voltage signal received from the low pass filter into a first pulse signal and outputs the first pulse signal;
  a multiplexer which multiplexes the first pulse signal from the voltage/frequency converter and a second pulse signal from the central control block to generate a multiplexed signal and outputs the multiplexed signal; and
  a rotator controller which controls the rotator in response to the first pulse signal received from the voltage/frequency converter and the position of the rotator in response to the second pulse signal.

3. The apparatus of claim 1, wherein the position control block comprises:
  a position controller which receives a pulse signal from the central control block and controls the moving unit; and
  a limit sensor which senses an electromagnetic wave of a predetermined wavelength at the moving unit, generates a limit signal limiting the pulse signal, and outputs the limit signal to the central control block.

4. The apparatus of claim 1, wherein the energy source control block comprises:
  a first switch which receives power and generates a pulse signal;
  a pulse width modulation controller which receives a reference signal from the central control block and compares the reference signal with the pulse signal so as to adjust a duty ratio of the pulse signal; and
  a delay switch which receives a delay signal from the central control block, switches the pulse signal output from the first switch in a manner that a resulting switched pulse signal corresponds to the delay signal, and provides the switched pulse signal to the energy source.

5. The apparatus of claim 4, wherein the energy control block further comprises:
  an inductor which maintains the pulse signal at a consistent level, the inductor being disposed between the first switch and the delay switch; and
  a capacitor, wherein the inductor is connected in parallel with the capacitor.

6. The apparatus of claim 4, wherein the energy source control block further comprises a cooler which reduces heat generated from the energy source by exhausting the heat to the outside.

7. The apparatus of claim 1, wherein the detector control block comprises:
  an amplifier which amplifies a signal detected at the detector; and
  an analog-to-digital converter which converts the signal amplified by the amplifier into a digital signal and outputs the digital signal to the central control block.

8. An apparatus for controlling a microfluidic system, wherein the microfluidic system comprises a microfluidic device in which a microfluidic structure is arranged on a rotary body; a rotator which rotates the rotary body; a moving unit which moves from a first position to a second position of the microfluidic device; and an energy source; the apparatus comprising:
  a central control block which controls operation of the microfluidic system;
  a rotator control block which controls the rotator in response to a first control signal from the central control block, a position control block which controls a position of the moving unit in response to a second control signal from the central control block; and
  an energy source control block which controls an emission of energy from the energy source in response to a third control signal from the central control block, wherein the energy source emits an electromagnetic wave, wherein the moving unit moves the energy source from the first position to the second position in the direction of a radius of the microfluidic apparatus, and
  wherein the position control block comprises:
    a position controller which receives a pulse signal from the central control block and controls the moving unit; and
    a limit sensor which senses an electromagnetic wave of a predetermined wavelength at the moving unit, generates a limit signal limiting the pulse signal, and outputs the limit signal to the central control block.

* * * * *